United States Patent [19]

Chamberlin, Sr.

[11] Patent Number: Plant 6,007

[45] Date of Patent: Sep. 8, 1987

[54] PEACH TREE, SUMMER SUN

[75] Inventor: Thomas O. Chamberlin, Sr., Visalia, Calif.

[73] Assignee: H. P. Metzler & Sons, Del Rey, Calif.

[21] Appl. No.: 788,132

[22] Filed: Oct. 16, 1985

[51] Int. Cl.[4] ..... A01H 5/00

[52] U.S. Cl. ..... Plt./43

[58] Field of Search ..... Plt./43

*Primary Examiner*—James R. Feyrer

*Attorney, Agent, or Firm*—Worrel & Worrel

[57] ABSTRACT

A new and distinct peach tree denominated varietally as "Summer Sun", generally resembling the June Lady Peach Tree (unpatented), but bearing a freestone fruit having a yellow, firm, and crisp flesh, and which is mature for harvesting approximately 15 through 20 June, later than that of the June Lady Peach Tree.

1 Drawing Figure

BACKGROUND OF THE NEW VARIETY

The present invention relates to a new and distinct variety of peach tree, denominated varietally as "Summer Sun", which is generally similar in characteristics to the "June Lady" Peach Tree (unpatented), of which it is a newly found seedling, but from which it is distinguished as to novelty by bearing freestone fruit which are ripe for picking approximately from the 15th through the 20th of June.

The June Lady Peach Tree is well known as a vigorous producer of large, firm-fleshed and clingstone fruit which is ripe for harvesting approximately mid-June in the San Joaquin Valley of Central California. Further, the fruit of the June Lady Peach Tree has long been known for its excellent eating quality and delicious flavor.

It has long been recognized that it would be desirable to have a peach tree generally resembling the June Lady Peach Tree, which bears fruit which ripens for eating later in the season, whereby the commercial demand of a large, yellow-fleshed peach can effectively be satisfied over a greater period of time.

ORIGIN AND ASEXUAL REPRODUCTION OF THE NEW VARIETY

For decades, the inventor has devoted much of his time to the development of new and different varieties of fruit trees. Pursuant to this purpose, the inventor has consistently searched the orchards of his employer in an attempt to locate a peach tree which is similar in characteristics to the June Lady Peach tree, but which ripens later in the season. The new "Summer Sun" variety, was a newly found seedling of the June Lady Peach Tree. The seeds which produced this newly found seedling were planted in the nursery of the applicant's employer, H. P. Metzler and Sons of Del Rey, Calif., during the winter of 1975–1976. The first fruit was produced by these new seedlings in 1978. After producing fruit, the inventor permitted the subject peach tree to bear fruit for two more years before taking bud wood for test planting. It was observed during this period of time that the peaches produced by the subject peach tree had a firmness, color and shape that was desired by the inventor.

During the 1979 season, bud wood was collected from the seedlings and was used, during the winter of 1979–1980, for budding 30 stock trees in the H. P. Metzler and Sons test area. Over a period of years, the inventor was again able to confirm that the tree and fruit characteristics resulting from such budding, was identical to that of the original seedling.

SUMMARY OF THE NEW VARIETY

The instant variety of peach tree is characterized by perpetuating many of the desirable characteristics of the June Lady Peach Tree, but has the important distinction of bearing fruit ripe for harvesting approximately June 15 through June 20, which is later than the June Lady Peach Tree. The fruit of the subject invention is freestone in nature, having a flesh which is bright yellow with very little, or no red in the pit cavity at picking time. In addition, the blossom and leafing of the subject variety tree takes place a few days before the Springcrest Peach, which is one of the earliest blooming trees in the San Joaquin Valley of Central California.

BRIEF DESCRIPTION OF THE DRAWING

The accompanying drawing is a color photograph of four mature fruit of the subject variety, one of which has been divided in the suture plane to show the flesh, stone and pit cavity characteristics; together with a twig bearing representative leaves, which display the dorsal and ventral coloration thereof.

DETAILED DESCRIPTION

Referring more particularly to the pomological details of this new and distinct variety of peach tree, the following has been observed under the ecological conditions prevailing at the orchard of the inventor's employer, H. P. Metzler & Sons, in Del Rey, Calif. All major color code plate identifications are by reference to the Inter-Society Color Council, National Bureau of Standards. However, common color names are also used occasionally.

TREE

Vigor: Vigorous.

Productivity: Productive.

Figure: Normal, depending upon pruning practices.

Size: Normal.

Trunk:

*Diameter in relation to length.*—Average.

Bark:

*Texture.*—Average, approximately 15 lenticels per square inch; lenticel color — 47 D.gy.R.Br.

Regularity of bearing: Regular.

Branches:

*Size.*—Average.

*Surface texture.*—Average.

*Color.*—47D. gy R. Br.

*Lenticels.*—Number approximately 15 per square inch; Size — Medium.

Leaves:

*Size.*—Average.

*Length.*—177.8 mm.

*Width.*—38.1 through 44.45 mm.

*Color.*—Ventral surface — 127 gy.01G; Dorsal surface — 122 gy. y. G.

*Marginal form.*—Serrate.

*Leaf glands.*—Reniform.

*Petiole.*—Length — 12.7 mm. Thickness — 2.381 mm.

*Stem glands.*—Number — Average number 4; Arrangement — paired, usually opposite to each other.

Flower buds:

*Size.*—Medium.

*Length.*—7.938 mm., this length is determined at a time before color appears on the tip of the bud.

*Length.*—14.288 mm., this length is determined at the time when the bud reaches its red stage with the stamen showing.

*Diameter.*—6.35 mm.

*Shape.*—Rounded to slightly elongated.

Flowers:

*Date of bloom.*—25 Feb. through 1 Mar., in Del Rey, Calif.

*Size.*—Small.

*Diameter for each petal.*—4.762 mm.

*Length for each petal.*—9.525 mm.

*Color.*—Light Pink edge, 247 Sp.Pk.; Central Portion — Very Light Pink, 4.L.Pink.

FRUIT

Maturity: 15 through 20 June for harvesting in Del Rey, Calif.

Size: Medium.

Uniformity: Exceptional.

*Average cheek diameter.*—60.325 through 76.2 mm.

*Diameter transverse in the suture plane.*—Approximately 76.2 mm.

*Average axial diameter.*—Approximately 76.2 mm.

Form:

*Symmetry.*—Symmetrical.

*Uniformity.*—Exceptional.

*Suture.*—Distinct, smooth. Length — approximately 95.25 mm. Position — extending from the base to the apex.

*Ventral surface.*—Rounded to slightly flat.

*Stem cavity.*—Slightly elongated to round. Length — approximately 5.525 mm.

*Base.*—Wide and flat.

*Apex.*—Rounded, occasionally flat.

*Pistil point.*—Small, sometimes slightly depressed.

Stem:

*Length.*—9.525 mm.

*Thickness.*—Approximately 3.175 mm.

Skin:

*Thickness.*—Approximately 1.791 mm.

*Texture.*—Smooth, tough, tenacious to flesh.

*Tendency to crack.*—None observed.

*Color.*—Very Dark Red to Softer Red with some Yellow; Dark Red — 41 deep r. Br.; Softer Red — 14 v. deep red; Yellow — 82 V. Y.

*Pubescence.*—Average.

Flesh:

*Color.*—Yellow, 83 brill. Y.

*Surface texture of pit well.*—Rough.

*Color of pit well.*—Yellow, 83 brill, Y. with occasional hues of red; 11.V.Red.

*Amygdalin.*—Lacking.

*Juice.*—Very good quality, with a hint of tartness.

*Flavor.*—Excellent, crisp.

*Aroma.*—Slight.

*Texture.*—Smooth and crisp.

*Fibers.*—None evident.

*Ripening.*—Even.

*Eating quality.*—Good.

Stone:

*Adhesion.*—Full freestone.

*Fibers.*—None evident.

*Size.*—Average. Length — Approximately 31.75 mm.; Width — Approximately 25.40 mm.; Thickness — Approximately 22.225 mm.

*Form.*—Roundish in appearance, however, slightly elongated.

*Base.*—Flat and slightly narrow.

*Texture of sides.*—Rough.

*Ridges.*—Medium to heavy in number, irregular.

Use: Fresh Market.

Keeping quality: Excellent.

Shipping quality: Excellent.

Resistance to disease: Unknown.

Although the new variety of peach tree possesses the desirable characteristics noted under the growing conditions prevailing in Del Rey, Calif., in the central portion of the San Joaquin Valley, it is to be understood that variations of the usual magnitude in characteristics incident to changes in growing conditions, fertilization, pruning and pest control are to be expected.

Having thus described and illustrated my new variety of peach tree, what I claim as new and desire to secure by Plant Letters Patent is:

1. A new and distinct variety of peach tree substantially as illustrated and described, characterized by its bearing freestone fruit having a yellow flesh and by its general resemblance to the June Lady Peach Tree (unpatented), but from which it is distinguished by its bearing of fruit which mature for harvesting approximately 15 through 20 June, later than that of the June Lady Peach Tree, and having a flesh which is firm and crisp with a skin which is tenacious to flesh.

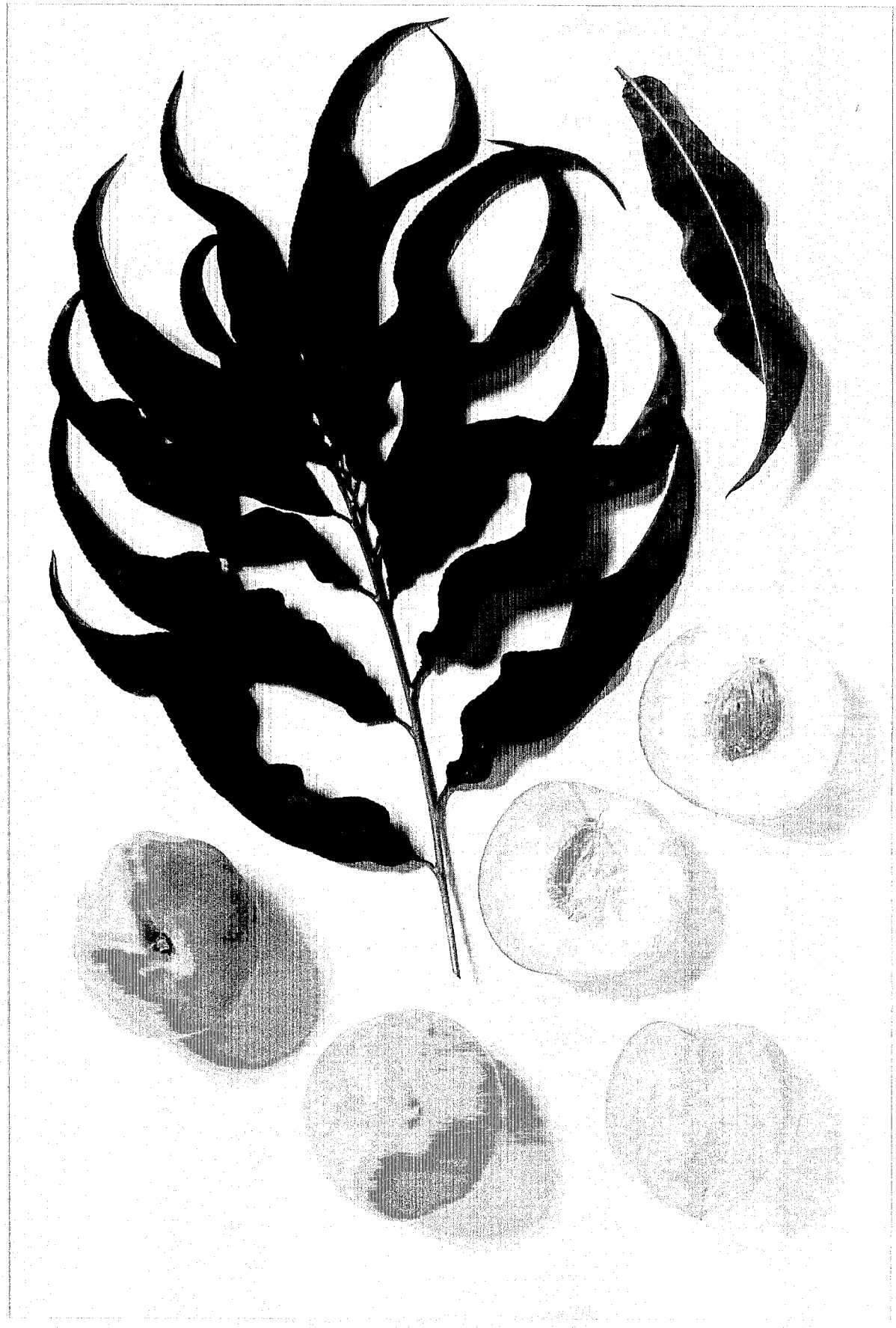

* * * * *